United States Patent
Suemori et al.

(10) Patent No.: US 11,505,785 B2
(45) Date of Patent: Nov. 22, 2022

(54) CELL CULTURE METHOD USING LAMININ FRAGMENT-CONTAINING MEDIUM

(71) Applicant: Kyoto University, Kyoto (JP)

(72) Inventors: Hirofumi Suemori, Kyoto (JP); Takamichi Miyazaki, Kyoto (JP)

(73) Assignee: Kyoto University, Kyoto (JP)

( * ) Notice: Subject to any disclaimer, the term of this patent is extended or adjusted under 35 U.S.C. 154(b) by 218 days.

(21) Appl. No.: 15/771,329

(22) PCT Filed: Nov. 8, 2016

(86) PCT No.: PCT/JP2016/083014
§ 371 (c)(1),
(2) Date: May 10, 2018

(87) PCT Pub. No.: WO2017/082220
PCT Pub. Date: May 18, 2017

(65) Prior Publication Data
US 2018/0334656 A1 Nov. 22, 2018

(30) Foreign Application Priority Data

Nov. 10, 2015 (JP) .............................. JP2015-219996

(51) Int. Cl.
*C12N 5/074* (2010.01)
*C12N 5/00* (2006.01)
*C12N 5/0735* (2010.01)

(52) U.S. Cl.
CPC ............. *C12N 5/0696* (2013.01); *C12N 5/00* (2013.01); *C12N 5/0606* (2013.01); *C12N 2500/30* (2013.01)

(58) Field of Classification Search
CPC ...... A61K 35/545; C12N 5/00; C12N 5/0696; C12N 5/0606; C12N 2500/30; C12N 2502/45
See application file for complete search history.

(56) References Cited

U.S. PATENT DOCUMENTS

| | | | |
|---|---|---|---|
| 4,565,789 A | 1/1986 | Liotta et al. | |
| 2010/0129910 A1* | 5/2010 | Evseenko | 435/383 |
| 2012/0220031 A1* | 8/2012 | Sekiguchi | C12N 5/0696 435/366 |
| 2014/0127806 A1* | 5/2014 | Sekiguchi | 435/377 |
| 2016/0137965 A1 | 5/2016 | Sekiguchi et al. | |

FOREIGN PATENT DOCUMENTS

| | | | |
|---|---|---|---|
| CN | 105378054 A | 3/2016 | |
| EP | 3 009 502 A1 | 4/2016 | |
| JP | 6-219961 A | 8/1994 | |
| WO | WO 2011/043405 A1 | 4/2011 | |
| WO | WO 2013/047763 A1 | 4/2013 | |
| WO | WO 2014/199754 A1 | 12/2014 | |
| WO | WO-2015080297 A1 * | 6/2015 | ............ A61K 35/30 |
| WO | WO 2015/111686 A1 | 7/2015 | |
| WO | WO 2016/067629 A1 | 5/2016 | |

OTHER PUBLICATIONS

Hall et al., "Laminin enhances the growth of human neural stem cells in defined culture media", 2008, BMC Neuroscience 9(71), p. 1-10.*
Corning, "Surface Areas and Recommended Medium Volumes for Corning® Cell Culture Vessels", 2012, Electronic Resource, [https://www.corning.com/catalog/cls/documents/application-notes/CLS-AN-209.pdf], Retrieved on May 13, 2020.*
Hall, Peter E. et al., "Laminin enhances the growth of human neural stem cells in defined culture media" BMC Neuroscience, 2008, pp. 1-10, vol. 9, No. 71.
Office Action for Canadian Application No. 3,004,251 dated Feb. 13, 2020.
Miyazaki, Takamichi et al., "Recombinant human laminin isoforms can support the undifferentiated growth of human embryonic stem cells" Biochemical and Biophysical Research Communications, 2008, pp. 27-32, vol. 375.
Miyazaki, Takamichi et al., "Laminin E8 fragments support efficient adhesion and expansion of dissociated human pluripotent stem cells" Nature Communications, 2012, pp. 1-10, vol. 3, No. 1236.
International Search Report for PCT/JP2016/083014 dated Nov. 30, 2016.
International Preliminary Report on Patentability for PCT/JP2016/083014.

* cited by examiner

*Primary Examiner* — Janet L Epps-Smith
*Assistant Examiner* — Alexander W Nicol
(74) *Attorney, Agent, or Firm* — Knobbe, Martens, Olson & Bear, LLP (57) ABSTRACT

Provided is a cell culture method comprising the step of culturing cells using a medium containing a laminin fragment having integrin binding activity, the method not comprising the step of coating a culture vessel with a laminin or a laminin fragment before seeding the cells in the culture vessel. The cell culture method of the present invention uses a smaller amount of a laminin fragment and still achieves a comparable culture efficiency as compared with the conventional cell culture method that uses a culture vessel precoated with a laminin or a laminin fragment.

5 Claims, 4 Drawing Sheets

CELL CULTURE METHOD USING LAMININ FRAGMENT-CONTAINING MEDIUM

CROSS REFERENCE TO RELATED APPLICATIONS

This application is a U.S. National Phase Application of PCT International Application Number PCT/JP2016/083014, filed on Nov. 8, 2016, designating the United States of America and published in the Japanese language, which is an International Application of and claims the benefit of priority to Japanese Patent Application No. 2015-219996, filed on Nov. 10, 2015. The disclosures of the above-referenced applications are hereby expressly incorporated by reference in their entireties.

TECHNICAL FIELD

The present invention relates to a cell culture method using a medium containing a laminin fragment and to a cell culture medium containing a laminin fragment.

BACKGROUND ART

Human pluripotent stem cells, such as human ES cells and human iPS cells, are receiving worldwide attention for their potential application to regenerative medicine. In order to realize the application of human pluripotent stem cells to regenerative medicine, there is a need to develop culture techniques for culturing and propagating such stem cells in a safe and stable manner.

The present inventors examined the type of integrins expressed on human ES cells, and reported that α6β1 integrin is a major adhesion receptor of human ES cells and that recombinant human laminins (particularly, laminin 332 composed of α3, β3 and γ2 chains, and laminin 511 composed of α5, β1 and γ1 chains) are useful as a feeder-free culture substrate for human ES cells (see Non Patent Literature 1). The present inventors also found that the use of a laminin 511E8 fragment (laminin 511E8) as a feeder-free culture substrate enables passage culture of human pluripotent stem cells in a dissociated single-cell state, which had been previously difficult (see Patent Literature 1 and Non Patent Literature 2).

Currently, a recombinant human laminin 511E8 fragment is commercially available (trade name: iMatrix-511, Nippi Inc.), and the use of human laminin 511E8 as a culture substrate for human pluripotent stem cells, such as human ES cells and human iPS cells, is rapidly spreading. However, cell culture using human laminin 511E8 as a substrate conventionally requires precoating the surface of a culture vessel with a large amount of human laminin 511E8. Such a conventional culture method is costly, and therefore, disadvantageous. In addition, the process for culture substrate coating usually involves adding a culture substrate solution prepared using phosphate buffer etc. to a culture vessel, followed by incubation at about 4° C. to about 37° C. for a few hours to overnight. Therefore, if a low-cost, coating-free protocol for cell culture can be provided, human laminin 511E8 would be more widely used as a culture substrate for pluripotent stem cells.

CITATION LIST

Patent Literature

Patent Literature 1: WO 2011/043405

Non Patent Literature

Non Patent Literature 1:
Miyazaki T, Futaki S, Hasegawa K, Kawasaki M, Sanzen N, Hayashi M, Kawase E, Sekiguchi K, Nakatsuji N, Suemori H. Recombinant human laminin isoforms can support the undifferentiated growth of human embryonic stem cells. Biochem. Biophys. Res. Commun. 375:27-35, 2008.

Non Patent Literature 2:
Miyazaki T, Futaki S, Suemori H, Taniguchi Y, Yamada M, Kawasaki M, Hayashi M, Kumagai H, Nakatsuji N, Sekiguchi K, Kawase E. Laminin E8 fragments support efficient adhesion and expansion of dissociated human pluripotent stem cells. Nat Commun. 3, 1236. Doi: 10.1038/ncomms2231, 2012.

SUMMARY OF INVENTION

Technical Problem

An object of the present invention is to provide a cell culture method that uses a smaller amount of a laminin fragment and still achieves a comparable culture efficiency as compared with the conventional cell culture method that uses a culture vessel precoated with a laminin or a laminin fragment (precoating method).

Solution to Problem

In order to achieve the above-mentioned object, the present invention includes the following.
(1) A cell culture method comprising the step of culturing cells using a medium containing a laminin fragment having integrin binding activity, the method not comprising the step of coating a culture vessel with a laminin or a laminin fragment before seeding the cells in the culture vessel.
(2) The cell culture method according to the above (1), wherein the cells are seeded and cultured in a culture vessel which is not precoated with a laminin or a laminin fragment.
(3) The cell culture method according to the above (1) or (2), wherein the laminin fragment having integrin binding activity is a laminin E8 fragment.
(4) The cell culture method according to any one of the above (1) to (3), wherein the laminin fragment is present in the medium at such a concentration that a predetermined volume of the medium in the culture vessel contains 0.03 μg to 2 μg of the laminin fragment per $cm^2$ of culture surface area of the culture vessel.
(5) The cell culture method according to the above (4), wherein the laminin fragment is present in the medium at such a concentration that a predetermined volume of the medium in the culture vessel contains 0.06 μg to 0.5 μg of the laminin fragment per $cm^2$ of culture surface area of the culture vessel.
(6) The cell culture method according to any one of the above (1) to (5), wherein the integrin is integrin α6β1, integrin α6β4, integrin α3β1 and/or integrin α7β1.
(7) The cell culture method according to any one of the above (1) to (6), wherein the cells are mammalian cells.
(8) The cell culture method according to the above (7), wherein the cells are mammalian stem cells or cells differentiated from the stem cells. (9) The cell culture method according to the above (8), wherein the cells are pluripotent stem cells. (10) A cell culture medium containing a laminin fragment having integrin binding activity.

(11) The cell culture medium according to the above (10), wherein the laminin fragment is present at a concentration of 0.15 μg/mL to 10 μg/mL.

Advantageous Effects of Invention

The present invention provides a cell culture method that uses a smaller amount of a laminin fragment and still achieves a comparable culture efficiency as compared with the conventional precoating method. Also provided is a cell culture medium for use in such a cell culture method. The cell culture method of the present invention does not need precoating a culture vessel with a laminin fragment, and thus can shorten the time required for cell culture. In addition, the reduced amount of the laminin fragment used leads to a lower culture cost. Moreover, personal errors in the coating results can be eliminated, and thus, a simple culture method independent of individual cell culture skills can be provided.

BRIEF DESCRIPTION OF DRAWINGS

FIG. 1A shows the results for H9 human ES cells and FIG. 1B shows the results for 253G1 human iPS cells.

DESCRIPTION OF EMBODIMENTS

Cell Culture Method

The cell culture method of the present invention comprises the step of culturing cells using a medium containing a laminin fragment having integrin binding activity (hereinafter may be referred to simply as a "laminin fragment"), the method not comprising the step of coating a culture vessel with a laminin or a laminin fragment before seeding the cells in the culture vessel. That is, the culture method of the present invention does not need the step of coating a culture vessel, which step is essential for the conventional precoating method.

The culture vessel used in the culture method of the present invention is not particularly limited and any culture vessel can preferably be used. Specific examples include a culture vessel whose culture surface is not coated with anything, a culture vessel whose culture surface is coated with a culture substrate (extracellular matrix) and a culture vessel whose culture surface has been subjected to a treatment to facilitate cell adhesion, such as charging treatment. Preferably, a culture vessel which is not precoated with a laminin or a laminin fragment is used in the culture method of the present invention. The culture vessel which is not precoated with a laminin or a laminin fragment means a culture vessel whose culture surface is not precoated with a laminin (full-length laminin) or a laminin fragment (part of a full-length laminin). Examples of such a culture vessel include a culture vessel whose culture surface is not coated with anything, a culture vessel whose culture surface is coated with a culture substrate which is neither a laminin nor a laminin fragment, and a culture vessel whose culture surface has been subjected to a treatment to facilitate cell adhesion, such as a charging treatment. The material, shape and the like of the culture vessel used in the culture method of the present invention are not particularly limited, and for example, glass or plastic dishes, flasks, multiwell plates and culture slides can preferably be used. A culture bag made of polymer membrane can also be preferably used.

The culture method of the present invention may be, specifically, (a) a method comprising suspending cells in a laminin fragment-containing medium for preparation of a cell suspension, and seeding the cell suspension in a culture vessel;

(b) a method comprising suspending cells in a medium without a laminin fragment for preparation of a cell suspension, adding a laminin fragment to the cell suspension, and seeding the cell suspension in a culture vessel; or (c) a method comprising suspending cells in a medium without a laminin fragment for preparation of a cell suspension, seeding the cell suspension in a culture vessel, and adding a laminin fragment to the medium in the culture vessel.

Laminin is a heterotrimeric molecule consisting of three subunits termed α, β and γ chains. Five kinds of α chains (α1 to α5), three kinds of β chains (β1 to β3) and three kinds of γ chains (γ1 to γ3) are known, and various combinations of these chains give rise to at least 12 kinds of laminin isoforms (for example, "laminin α5β1γ1" is herein referred to as "laminin 511". The same will apply to other isoforms). The laminin fragment used in the culture method of the present invention is a laminin fragment having integrin binding activity. Such a laminin fragment is preferably a heterotrimeric laminin fragment. Specifically, the laminin fragment is composed of α, β and γ chains of which at least one chain, preferably at least two chains, more preferably all the three chains are shorter than the corresponding full-length chains. The heterotrimer formation of the laminin fragment can be confirmed from, for example, the number of bands detected by SDS-PAGE. The integrin binding activity of the laminin fragment can be confirmed by a solid phase binding assay etc.

The origin of the laminin is not particularly limited, and laminins of various organisms can be used. Preferred are laminins of mammals, including but not limited to humans, mice, rats, cattle and pigs. Among these, human laminins are particularly preferred. In the case where human stem cells are cultured for preparation of materials for human regenerative medicine, a xeno-free (the culture system contains no xenogeneic components) environment is required, and for this reason, human laminins are preferably used.

As the laminin fragment used in the culture method of the present invention, a laminin E8 fragment (hereinafter referred to as "laminin E8") is preferred in terms of the strength of the integrin binding activity and the efficiency of recombinant expression. The laminin E8 was identified as a fragment having stronger cell-adhesive activity among the fragments obtained by elastase digestion of mouse laminin 111 (Edgar D., Timpl R., Thoenen H. The heparin-binding domain of laminin is responsible for its effects on neurite outgrowth and neuronal survival. EMBO J., 3: 1463-1468, 1984; and Goodman S L., Deutzmann R., von der Mark K. Two distinct cell-binding domains in laminin can independently promote nonneuronal cell adhesion and spreading. J. Cell Biol., 105: 589-598, 1987). Elastase digestion of laminins other than mouse laminin 111 could presumably produce fragments corresponding to the mouse laminin 111E8, but there is no report on isolation or identification of such E8 fragments. Laminin E8 is a trimeric fragment composed of a C-terminal fragment of the α chain lacking globular domains 4 and 5 (hereinafter referred to as "α chain E8"), a C-terminal fragment of the β chain (hereinafter referred to as "β chain E8"), and a C-terminal fragment of the γ chain (hereinafter referred to as "γ chain E8"), and the molecular weight of the trimer is about 150 to 170 kDa. The α chain E8 generally consists of about 770 amino acids, of which about 230 amino acids from the N-terminus are involved in the trimer formation. The β chain E8 generally consists of about 220 to 230 amino acids. The γ chain E8 generally consists of about 240 to 250 amino acids. The laminin E8 used in the present invention does not have to be an elastase-digested product of laminins and may be any laminin fragment having a cell-adhesive activity, structure and molecular weight substantially equivalent to those of the mouse laminin 111E8.

The laminin fragment may be a native laminin fragment or a modified laminin fragment that has modification of one or more amino acid residues but retains biological activities of the native laminin. The method for producing the laminin fragment is not particularly limited. For example, the laminin fragment can be obtained by digestion of a full-length laminin purified from laminin-high-expressing cells with a protease such as elastase, followed by isolation and purification of the fragment of interest. Alternatively, the laminin fragment can be produced as a recombinant protein. In terms of production quantity, quality uniformity, production cost, etc., it is preferred that the laminin fragment is produced as a recombinant protein.

The recombinant laminin fragment can be produced by appropriate known recombinant techniques, for example, by preparing DNAs encoding partial-length laminin α, β and γ chains, inserting the DNAs into separate expression vectors, cointroducing the three resulting expression vectors into appropriate host cells, and purifying the expressed trimeric protein by a known method. The method for producing the recombinant laminin fragment (laminin E8) may be, for example, the method of Ido et al. (Ido, H et al., J. Biol. Chem. 282, 11144-11154, 2007.), but is not limited thereto. Information regarding the nucleotide sequences of the genes encoding α, β and γ chains which constitute laminins of major mammals and the amino acid sequences of these chains can be obtained from known databases (e.g., DDBJ, EMBL, GenBank, etc.). The recombinant laminin 511E8 is commercially available from Nippi Inc. under the trade name iMatrix-511, and this product can preferably be used.

The culture method of the present invention can preferably be used for culturing cells expressing a laminin-binding integrin. Examples of the laminin-binding integrin include integrin α6β1, integrin α6β4, integrin α3β1 and integrin α7β1. The cells to be cultured are preferably mammalian cells, and more preferably mammalian stem cells or cells in various stages of differentiation of stem cells towards somatic cells. The stem cells include somatic stem cells and pluripotent stem cells. Examples of the somatic stem cells include neural stem cells, mesenchymal stem cells, hematopoietic stem cells, cardiac stem cells, hepatic stem cells and small intestinal stem cells. Examples of the pluripotent stem cells include ES cells (embryonic stem cells), iPS cells (induced pluripotent stem cells), mGS cells (multipotent germ stem cells), hybridomas of ES cells and somatic cells, and MUSE cells. Examples of the mammal as the origin of the cells include humans, mice, rats, cattle and pigs. Particularly preferred are humans.

For example, human ES cells and human iPS cells predominantly express integrin α6β1, and therefore, in the case where a laminin isoform fragment having a high binding activity for integrin α6β1 is used in the present invention, provided is a culture method useful for culturing pluripotent stem cells with their pluripotency (undifferentiated state) being maintained. Examples of the laminin isoform having a high binding activity for integrin α6β1 include laminin 511, laminin 521, laminin 332 and laminin 111 (Matrix Biology 25 (2006), 189-197).

For example, human neural progenitor cells predominantly express integrin α3β1 or α7β1, and therefore, in the case where a laminin isoform fragment having a high binding activity for integrin α3β1 or α7β1 is used in the present invention, provided is a culture method useful for maintaining the adhesion and functions of cells in various stages of differentiation of pluripotent stem cells towards neural progenitor cells or of established neural progenitor cells. Examples of the laminin isoform having a high binding activity for integrin α3β1 or α7β1 include laminin 111, laminin 211, laminin 511 and laminin 521 (J Neurosci Res. 2006 April; 83(5):845-856, Matrix Biology 25 (2006), 189-197).

For example, myoblasts predominantly express integrin α7β1, and therefore, in the case where a laminin isoform fragment having a high binding activity for integrin α7β1 is used in the present invention, provided is a culture method useful for maintaining the adhesion and functions of cells in various stages of differentiation of pluripotent stem cells towards myoblasts or of established myoblasts. Examples of the laminin isoform having a high binding activity for integrin α7β1 include laminin 111 (J Cell Science 109, 3139-3150 (1996)).

For example, cardiomyocytes predominantly express integrins α3β1 and α6β1 in the early stage of differentiation, and the predominant type of integrin changes to integrin α7β1 as the differentiation progresses. Therefore, in the case where fragments of different laminin isoforms having a high binding activity for integrin α3β1, α6β1 or α7β1 are used as appropriate for the stage of differentiation, provided is a culture method useful for maintaining the adhesion and functions of cells in various stages of differentiation of pluripotent stem cells towards cardiomyocytes or of established cardiomyocytes. Examples of the laminin isoform having a high binding activity for integrin α3β1 or α6β1 include laminin 511, laminin 521 and laminin 332; and examples of the laminin isoform having a high binding activity for integrin α7(X2)β1 include laminin 211 and laminin 111 (Cardiovascular Research 47 (2000) 715-725).

For example, keratinocytes predominantly express integrin α6β4, and therefore, in the case where a laminin isoform fragment having a high binding activity for integrin α6β4 is used in the present invention, provided is a culture method useful for maintaining the adhesion and functions of cells in various stages of differentiation of pluripotent stem cells towards keratinocytes or of established keratinocytes. Examples of the laminin isoform having a high binding activity for integrin α6β4 include laminin 332 and laminin 511 (The Journal of biological chemistry 287 (22), 17975-17984, 2012).

Even in the case where cells have yet to be analyzed for their integrin expression in detail, as long as the cells have been found to express a specific type of laminin isoform in vitro or in vivo, a culture method useful for maintaining the adhesion and functions of such cells can be provided using a fragment of the corresponding laminin isoform. For example, vascular endothelial cells have been found to express laminin 411 and laminin 511, and adipocytes have been found to express laminin 411. Therefore, in the case where fragments of these laminin isoforms are used as appropriate for the cell type, provided is a culture method useful for maintaining the adhesion and functions of vascular endothelial cells or adipocytes.

The medium used in the culture method of the present invention is not particularly limited, and any appropriate medium for the cells to be cultured may be selected. A commercial or self-made medium may be used. The concentration of the laminin fragment in the medium is not particularly limited as long as the concentration is sufficient to achieve the desired adhesion efficiency of the cells to be cultured. Usually, the concentration of the laminin fragment in the medium is in such a range that a predetermined volume of the medium in the culture vessel contains 0.03 µg to 2 µg of the laminin fragment per $cm^2$ of culture surface area of the culture vessel, preferably 0.06 µg to 0.5 µg of the laminin fragment per $cm^2$ of culture surface area of the culture vessel, and more preferably 0.1 µg to 0.25 µg of the laminin fragment per $cm^2$ of culture surface area of the culture vessel. For example, when the volume of the medium at the time of seeding the cells in the culture vessel is 200 µL/$cm^2$ (culture surface area), 0.03 µg/$cm^2$ to 2 µg/$cm^2$ is equivalent to 0.15 µg/mL to 10 µg/mL, 0.06 µg/$cm^2$ to 0.5 µg/$cm^2$ is equivalent to 0.3 µg/mL to 2.5 µg/mL, and 0.1 µg/$cm^2$ to 0.25 µg/$cm^2$ is equivalent to 0.5 µg/mL to 1.25 µg/mL.

The present inventors have confirmed that the culture method of the present invention achieves a level of cell-adhesion efficiency and cell-growth rate comparable to that in the precoating method although the amount of the laminin fragment used per unit area of the culture surface is smaller than that in the precoating method (see Examples). Therefore, the culture method of the present invention is advantageous over the conventional method due to the reduced cost as well as the shortened culture time and the simple culture procedure. In addition, in the precoating method, which involves seeding cells in a culture vessel precoated with a laminin fragment, the cells adhere to the laminin fragment with which the cells come into first contact, resulting in non-uniform distribution of the cells on the culture surface. The culture method of the present invention can solve such a problem of the precoating method and achieves uniform distribution of the cells on the culture surface.

The first embodiment of the present invention comprises the steps of:
preparing a cell suspension using a laminin fragment-containing medium,
seeding the prepared cell suspension in a culture vessel, and
culturing the cells on appropriate conditions for the cells.

The second embodiment of the present invention comprises the steps of:
preparing a cell suspension using a medium without a laminin fragment,
adding a laminin fragment to the prepared cell suspension,
seeding the cell suspension containing the laminin fragment in a culture vessel, and
culturing the cells on appropriate conditions for the cells.

The third embodiment of the present invention comprises the steps of:
preparing a cell suspension using a medium without a laminin fragment,
seeding the prepared cell suspension in a culture vessel,
adding a laminin fragment to the cell suspension seeded in the culture vessel, and
culturing the cells on appropriate conditions for the cells.

All the procedures of the cell culture method of the present invention are well-known and easy for the skilled person to practice.

An embodiment of the culture method of the present invention where human pluripotent stem cells are cultured will be described below. Example of the medium used in the case of culturing human ES cells or human iPS cells include TeSR-E8 (trade name, STEMCELL Technologies Inc.), StemFit AK03N (trade name, Ajinomoto Co., Inc.), StemFit AK02N (trade name, Ajinomoto Co., Inc.), mTeSR1 (trade name, STEMCELL Technologies Inc.), TeSR2 (trade name, STEMCELL Technologies Inc.), StemPro hESC SFM (trade name, Thermo Fisher Scientific Inc.), NutriStem (trade name, Stemgent, Inc.), PSGro-free Human iPSC/ESC Growth Medium (trade name, StemRD), StemEZ (trade name, Cellagen Technology), Essential 8 (trade name, Thermo Fisher Scientific Inc.), PluriSTEM Human ES/iPS Medium (trade name, Millipore), PeproGrow hESC Embryonic Stem Cell Media (trade name, PeproTech, Inc.), L7 hPSC Media (trade name, Lonza), StemMACS (trade name, Milteny Biotech), HyCell-Stem Media (trade name, HyClone), DEF-CS 500 (trade name, Cellartis), S-Medium (trade name, DS Pharma Biomedical Co., Ltd.), Repro XF (trade name, ReproCELL Inc.) and StemSure hPSC Medium Δ (trade name, Wako Pure Chemical Industries, Ltd.).

(1) Collection of Human Pluripotent Stem Cells from Co-culture System with Feeder Cells To a culture dish in which human pluripotent stem cells have been co-cultured with feeder cells (for example, MEFs) (Day 3 to Day 5), a cell detachment solution (for example, Dissociation Solution for Primate ES Cells (RCHETP002, ReproCELL Inc.), 1 mg/mL dispase/DMEM-F12, 10 mg/mL collagenase IV/DMEM-F12, etc.) (for example, 1 mL/60 mm dish) is added, and incubation is performed at 37° C. for 5 minutes. The human pluripotent stem cells and the MEFs are detached from the culture dish and transferred into a 15-mL centrifuge tube. To this tube, about 10 mL of a medium is added, the cells are suspended, the tube is left to stand for 5 minutes to allow only the colonies to sediment, and then the supernatant is removed. By repeating this procedure twice or more, only colonies of human pluripotent stem cells are collected.

(2) Dissociation of Human Pluripotent Stem Cells into Single Cells

The collected human pluripotent stem cell colonies are dissociated into single cells. The method for single-cell dissociation is not particularly limited. For example, the human pluripotent stem cell colonies are incubated in an EDTA solution and then mechanically dissociated into single cells by several times of flushing using a Pipetman.

(3) Feeder-free Culture of Human Pluripotent Stem Cells (Precoating Method)

The single dissociated human pluripotent stem cells prepared from the co-culture system with feeder cells, or alternatively, single dissociated human pluripotent stem cells prepared from feeder-free culture system via detachment and dissociation steps are suspended in a medium containing a ROCK inhibitor at 10 µM. The cells are then seeded in, for example, a culture vessel precoated with 0.5

μg/cm² laminin 511E8 at a seeding density of about 1×10⁴ to 2×10⁴ cells/cm² (the cell number varies depending on the medium used). The culture is performed in an appropriate $CO_2$ concentration for the medium used. The replacement of the medium is performed daily or performed as described in the instruction manual for the medium used.

The cells are passaged at the time when the culture surface area available for cell expansion becomes limited or cell death becomes noticeable in the colonies. The method for passage culture is not limited. For example, a cell detachment and dissociation solution (for example, 5 mM EDTA solution) is added to the culture vessel, incubation is performed at room temperature for about 5 to 8 minutes, and the human pluripotent stem cells are detached and dissociated. The incubation time is selected as appropriate for the medium used. After complete detachment of the cells by several times of flushing, a medium is added for neutralization and dilution. The cells are collected into a centrifuge tube and then centrifuged (1000×g, 3 minutes). The cells are suspended in a fresh medium and seeded in, for example, a laminin 511E8-precoated culture vessel. The culture substrate used in the precoating method is not limited to laminin 511E8.

(4) Shift to Culture Method of Present Invention

The human pluripotent stem cells maintained in the co-culture system with feeder cells or in the precoating method are detached and dissociated. Then, the cells are suspended in a medium containing about 1.25 μg/mL laminin 511E8 and the cell suspension is seeded in a volume of about 200 μL/cm² (culture surface area) in a culture dish at a seeding density of about 1×10⁴ to about 2×10⁴ cells/cm². The seeding cell number is selected as appropriate for the medium used and is not limited to the above-mentioned range. The medium used at the time of cell seeding should contain a ROCK inhibitor at 10 μM, but the medium used at and after medium replacement does not have to contain a ROCK inhibitor. The culture is performed in an appropriate $CO_2$ concentration for the medium used. The replacement of the medium is performed daily or performed as described in the instruction manual for the medium used. In an alternative procedure, the cells are suspended in a medium without any laminin fragment, and after seeding, a laminin 511E8 solution is added at a final concentration of about 1.25 μg/mL. Human pluripotent stem cells are preferably in a single-cell state when seeded, but may be partially in clumps when seeded.

Medium

The present invention provides a cell culture medium containing a laminin fragment having integrin binding activity. The type of laminin fragment having integrin binding activity and the type of basic medium that can be used in the medium of the present invention are as described above. The concentration of the laminin fragment in the medium is usually selected from the range of 0.15 μg/mL to 10 μg/mL and is preferably 0.3 μg/mL to 2.5 μg/mL, more preferably 0.5 μg/mL to 1.25 μg/mL. When the medium of the present invention is used, the cell culture method of the present invention does not need the step of self-making a laminin fragment-containing medium by supplementation with a laminin fragment. In addition, since a laminin fragment-containing medium with a constant quality can be used, the quality of cultured cells can easily be controlled in the cell culture method of the present invention.

EXAMPLES

Hereinafter, the present invention will be illustrated in detail by examples, but the present invention is not limited thereto.

Experimental Materials (1) Extracellular Matrices iMatrix-511 was purchased from Nippi Inc. (#892011). Laminin 521 was purchased from BioLamina (#BLA-LN521-02). Vitronectin was purchased from Wako Pure Chemical Industries, Ltd. (#220-02041).

(2) Cells Used for Experiments

The human ES cells used were H9 cells purchased from National Stem Cell Bank. The human iPS cells used were 253G1 cells, which are a cell line established by the Center for iPS Cell Research and Application, Kyoto University. Each type of cells were maintained according to the organization's recommendations for co-culture with feeder cells, and then maintained according to a feeder-free culture method. After that, an aliquot of the cells was cultured according to an ordinary maintenance culture method, and another aliquot of the cells was cultured according to the culture method of the present invention (addition method).

Example 1

Comparison of Culture Substrate Concentration-Dependent Adhesion Efficiency of Human Pluripotent Stem Cells Between Cell Culture Method of Present Invention and Precoating Method In the precoating method, culture substrates iMatrix-511, laminin 521 and vitronectin were separately diluted in Dulbecco's PBS (DPBS) (Wako #045-29795) to such concentrations that the final coating concentrations would be 0 to 4 μg/cm². Each culture substrate solution was added in a volume of 50 μL/well to a 96-well microtiter plate (BD #351172), and the plate was allowed to stand at 37° C. in a $CO_2$ incubator for 3 hours for precoating treatment. On the other hand, in the cell culture method of the present invention (hereinafter referred to as "the method of the present invention"), precoating treatment was not performed. Instead, a solution of each culture substrate was directly added to a cell suspension at the time of cell passage.

At the time of cell passage, 5 mM EDTA/DPBS solution was added to the H9 human ES cells or the 253G1 human iPS cells, which had been maintained in TeSR-E8 medium under the same conditions as in the precoating method, and incubation was performed at room temperature for 5 to 8 minutes. The cells were detached and dissociated into single cells, and the cell number was counted. The cells were suspended in the medium (100 μL) at an appropriate concentration for seeding at 5×10⁴ cells/cm². To the wells for the precoating method, 10 μM Y-27632 was added. To the wells for the method of the present invention, 10 μM Y-27632 and an iMatrix-511 stock solution were added. The final iMatrix-511 concentrations were 0 to 2 μg/cm²/100 μL. After 24 hours, the culture supernatants were removed from the wells, and the wells were washed with warmed DMEM-F12 medium. The cells were fixed with 10% neutral buffered formalin for 10 minutes. The cells were treated with 100% ethanol for 10 minutes, and the plate was completely dried. The cells were stained with 10% Giemsa's solution/90% Milli-Q water for 1 hour. The plate was washed with Milli-Q water twice and completely air-dried. The cells were then lysed with a 1% aqueous SDS solution. The absorbance at a wavelength of 560 nm was measured with a multiplate reader.

Figure 1:
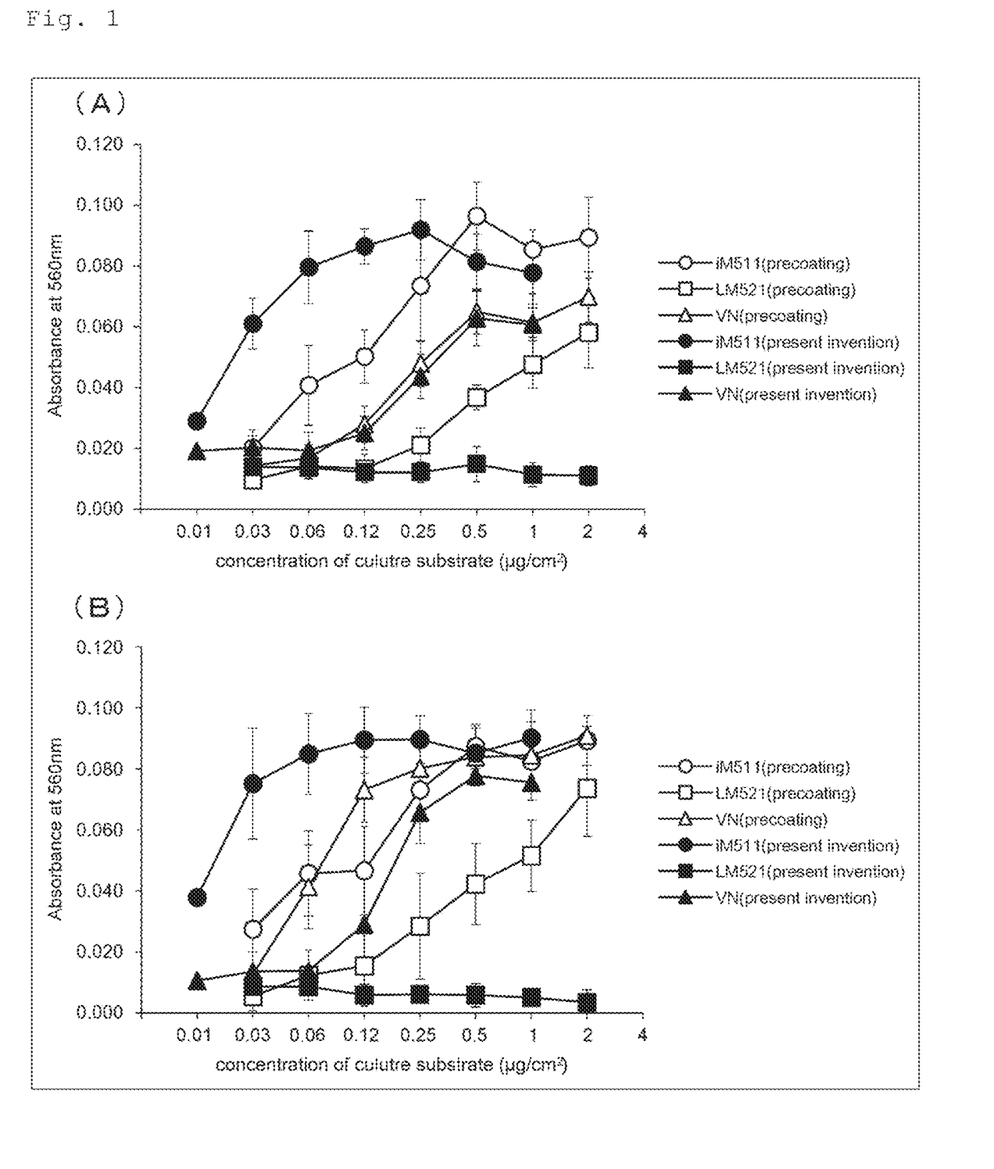
FIGS. 1A and 1B show the comparison of the culture substrate concentration-dependent adhesion efficiency of human pluripotent stem cells between the cell culture method of the present invention and the precoating method.

The results are shown in FIGS. 1A and 1B. FIG. 1A shows the results for H9 human ES cells and FIG. 1B shows the results for 253G1 human iPS cells. As is clear from FIG. 1A, for the precoating method, the maximum adhesion of the H9 human ES cells cultured on iMatrix-511 (iM511 in the figure) was comparable or superior to that on vitronectin (VN in the figure), and much superior to that on laminin 521 (LM521 in the figure). For the method of the present invention, the maximum adhesion of the H9 human ES cells cultured in the presence of iMatrix-511 was comparable to that in the precoating method, but the concentration of iMatrix-511 at the maximum adhesion was lower than that in the precoating method. As is clear from FIG. 1B, for the precoating method, the maximum adhesion of the 253G1 human iPS cells cultured on iMatrix-511 was comparable to that on vitronectin, and much superior to that on laminin 521. For the method of the present invention, the maximum adhesion of the 253G1 human iPS cells cultured in the presence of iMatrix-511 was comparable to that in the precoating method, but the concentration of iMatrix-511 at the maximum adhesion was lower than that in the precoating method.

These results show that the method of the present invention more efficiently promotes cell adhesion even with use of a lower-concentration laminin fragment as compared with the precoating method.

Example 2

Adhesion and Morphology of Human Pluripotent Stem Cells Cultured by Cell Culture Method of Present Invention or by Precoating Method The adhesion and morphology of the H9 human ES cells of Example 1 were observed under a microscope at 24 hours after seeding. For the precoating method, the wells for a culture substrate density of 1 µg/cm$^2$ were observed, and for the method of the present invention, the wells for a culture substrate density of 0.25 µg/cm$^2$ were observed. All the wells were observed before washed with the medium.

Figure 2:
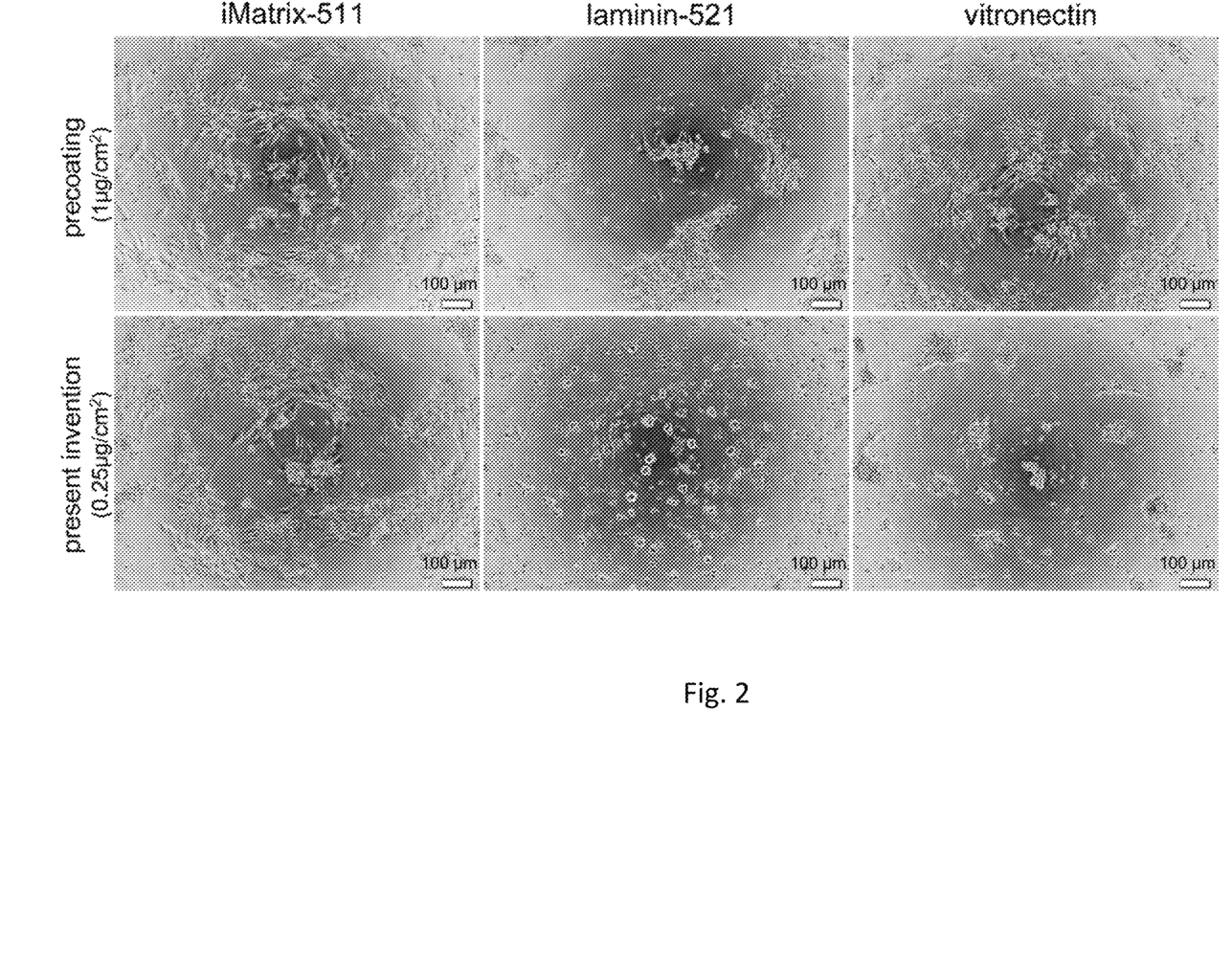
FIG. 2 is a set of images illustrating the adhesion and morphology of human pluripotent stem cells cultured by the cell culture method of the present invention or by the precoating method.

The results are shown in FIG. 2. The upper panels show the results for the precoating method, and the lower panels show the results for the cell culture method of the present invention. In each image, the scale bar marks 100 µm. As is clear from FIG. 2, the H9 human ES cells cultured in the presence of 0.25 µg/cm$^2$ iMatrix-511 by the method of the present invention showed a flat adherent morphology, which was similar to that of the cells cultured on 1 µg/cm$^2$ iMatrix-511 by the precoating method. That is, iMatrix-511 was effective at a lower concentration in the method of the present invention. In contrast, when laminin 521 was used at the indicated concentration in the method of the present invention, cell adhesion was not observed and some viable cells floated as cellular aggregates.

Example 3

Comparison of Growth Rate of Human Pluripotent Stem Cells between Method of Present Invention and Precoating Method The final coating concentration of iMatrix-511 was set to 1 µg/cm$^2$ in the precoating method. In the method of the present invention, an iMatrix-511 stock solution was added such that the amount of iMatrix-511 contained in a culture vessel would be 0.25 µg per cm$^2$ of culture surface area of the culture vessel.

To the H9 human ES cells, which had been maintained in TeSR-E8 medium, 5 mM EDTA/DPBS solution was added, and incubation was performed at room temperature for 5 minutes. The cells were detached and dissociated into single cells, and the cell number was counted. The cells were suspended in the medium at an appropriate concentration for seeding at $2\times10^4$ cells/cm$^2$. In the precoating method, 10 µM Y-27632 was added to the cell suspension, and this cell suspension was added to a precoated culture vessel. In the method of the present invention, the iMatrix-511 stock solution and 10 µM Y-27632 were added to the cell suspension, and this cell suspension was added to a coating-free culture vessel.

Figure 3:
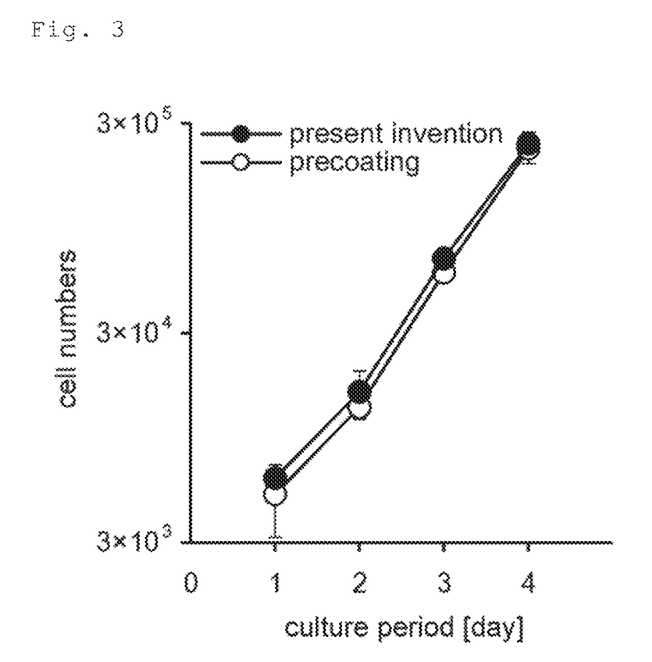
FIG. 3 shows the comparison of the growth rate of human pluripotent stem cells between the cell culture method of the present invention and the precoating method.

The graph of the growth rate is shown in FIG. 3. As is clear from FIG. 3, for the precoating method using 1 µg/cm$^2$ iMatrix-511 and for the method of the present invention using 0.25 µg/cm$^2$ iMatrix-511, similar cell adhesion was observed and then the cells were grown at a similar rate.

Figure 4:
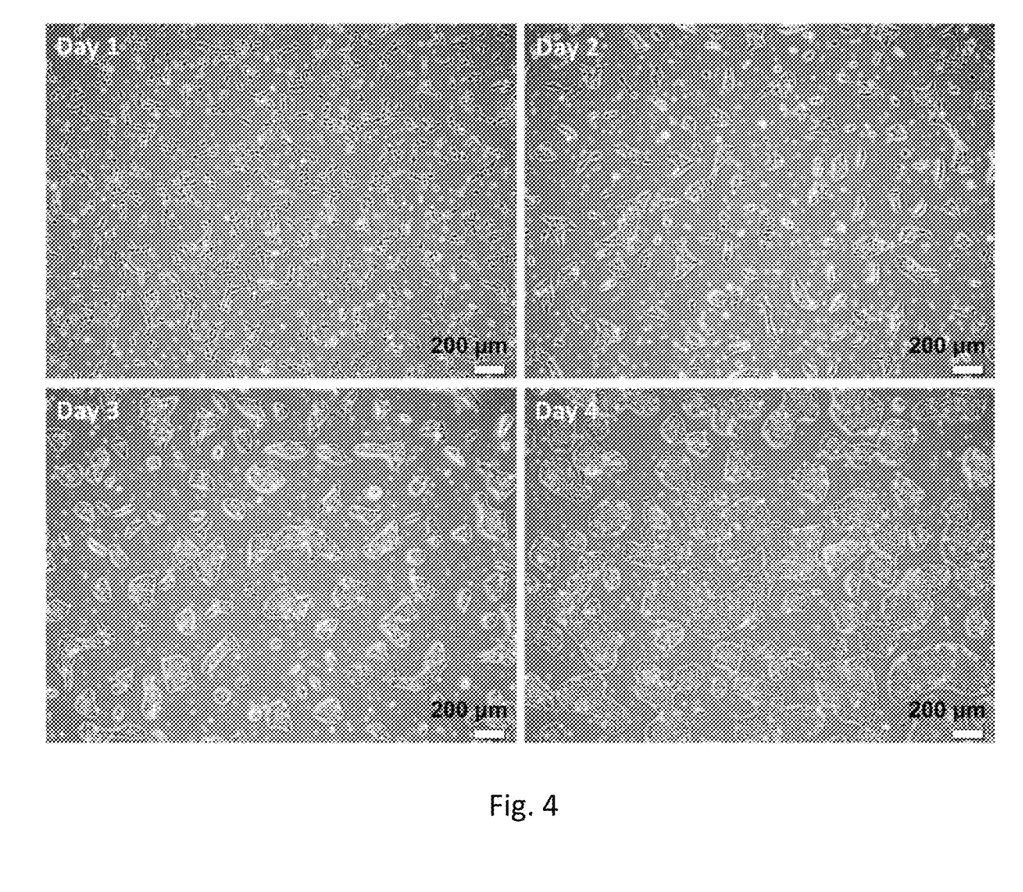
FIG. 4 a set of images illustrating the growth of human pluripotent stem cells cultured by the cell culture method of the present invention.

The growth of the H9 human ES cells cultured by the method of the present invention was observed under a microscope once daily from Day 1 (the starting day of the culture) to Day 4. The observation results are shown in FIG. 4. In each image, the scale bar marks 200 µm. As is clear from FIG. 4, the H9 human ES cells cultured by the method of the present invention showed stable adhesion and growth without detachment throughout the culture. These results show that the method of the present invention using iMatrix-511 allows cell growth at a rate as high as that in the precoating method although a smaller amount of iMatrix-511 was used than that in the precoating method.

The present invention is not limited to the particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A cell culture method comprising:
    culturing mammalian stem cells or cells differentiated from mammalian stem cells in a culture vessel comprising a medium, wherein said medium comprises a native laminin α5β1γ1 E8 fragment, wherein the native laminin α5β1γ1 E8 fragment is dissolved the medium at a concentration of 0.03 µg to 0.25 µg per cm$^2$ of culture surface area of the culture vessel, and wherein the method does not comprise coating the culture vessel with a laminin or a laminin fragment before seeding the mammalian stem cells or cells differentiated from mammalian stem cells in the culture vessel.

2. The cell culture method according to claim 1, wherein the mammalian stem cells are pluripotent stem cells.

3. The cell culture method according to claim 2, wherein the pluripotent stem cells are induced pluripotent stem cells (iPS cells).

4. The cell culture method according to claim 2, wherein the pluripotent stem cells are embryonic stem cells (ES cells).

5. A cell culture medium for mammalian stem cells or cells differentiated from the mammalian stem cells, comprising a native laminin α5β1γ1 E8 fragment, wherein the native laminin α5β1γ1 E8 fragment is dissolved in the cell culture medium at a concentration of 0.15 µg/mL to 1.25 µg/mL.

* * * * *